United States Patent [19]

Cohen

[11] Patent Number: 5,185,143
[45] Date of Patent: Feb. 9, 1993

US005185143A

[54] TERPOLYMER HAIR FIXATIVE RESINS PREPARED BY SOLUTION POLYMERIZATION OF MALEIC ANHYDRIDE, VINYL ACETATE AND ISOBORNYL ACRYLATE

[75] Inventor: Jeffrey M. Cohen, Fanwood, N.J.

[73] Assignee: ISP Investments Inc., Wilmington, Del.

[21] Appl. No.: 820,173

[22] Filed: Jan. 13, 1992

[51] Int. Cl.$^5$ .................. A61K 7/11; C08F 222/06; C08F 218/08; C08F 222/14
[52] U.S. Cl. ........................................ 424/47; 424/45; 424/78.33; 424/DIG. 1; 424/DIG. 2; 424/70; 424/71; 526/271; 526/281; 526/284; 526/328.5; 526/330
[58] Field of Search .......... 424/45, 47, 78.33, DIG. 2, 424/70, 71; 526/271, 281–284, 330

[56] References Cited

U.S. PATENT DOCUMENTS

| 4,689,379 | 8/1987 | Chuang ........................... 526/282 |
| 4,961,921 | 10/1990 | Chuang et al. ..................... 424/47 |
| 5,032,460 | 7/1991 | Kantner et al. .................... 528/23 |

Primary Examiner—Thurman K. Page
Assistant Examiner—E. J. Webman
Attorney, Agent, or Firm—Marilyn J. Maue; Walter Katz; Joshua J. Ward

[57] ABSTRACT

What is described herein is solution polymerization in acetone solvent of a monomer mixture of maleic anhydride, vinyl acetate and isobornyl acrylate or methacrylate.

6 Claims, No Drawings

TERPOLYMER HAIR FIXATIVE RESINS PREPARED BY SOLUTION POLYMERIZATION OF MALEIC ANHYDRIDE, VINYL ACETATE AND ISOBORNYL ACRYLATE

BACKGROUND OF THE INVENTION

1. Field of the Invention

This invention relates to terpolymer hair fixative resins suitable for use in pump and aerosol hair spray compositions, and, more particularly, to an improved method of making such terpolymer resins by solution polymerization of maleic anhydride, vinyl acetate and isobornyl acrylate and to esterified derivatives thereof.

2. Description of the Prior Art

Chuang, in U.S. Patent No. 4,689,379, described a one-step, aqueous suspension polymerization process for the preparation of terpolymers of vinyl acetate, mono-$C_4$-$C_5$ alkyl maleate and isobornyl acrylate in a molar ratio of about 1:0.35–1:0.05–0.25. The reaction mixture comprised particularly vinyl acetate, mono-n-butyl maleate and isobornyl acrylate.

Chuang, in U.S. Pat. No. 4,961,921, described another process for making the terpolymers disclosed in U.S. Pat. No. 4,689,379, having a relative viscosity of 1.10 to 1.30, by polymerizing a mixture of vinyl acetate, mono-n-butyl maleate and isobornyl acrylate as a solution in acetone solvent.

However, these processes are relatively slow requiring 8–20 hours for completion, because the monobutyl maleate reactant did not copolymerize rapidly with the other monomers. In addition, the terpolymer product of the prior art was the mono-alkyl maleate containing terpolymer only.

In view of the limitations of the prior art, it is an object of this invention to provide an improved process for making terpolymers suitable for use in pump and aerosol hair spray compositions, which is characterized by solution polymerization of a monomer mixture comprised of maleic anhydride, vinyl acetate and isobornyl acrylate.

Other features of the invention is the provision of a solution polymerization process in acetone solvent for preparing such terpolymers, which process can be carried to completion in about half the time required of solution polymerization processes employing mono-alkyl maleate as monomer reactant, and which can afford the terpolymer product independently in the form of either the free acid, an ester thereof, or as a hydrolyzed or neutralized derivative thereof.

These and other objects and features of the invention will be made apparent from the following description thereof.

SUMMARY OF THE INVENTION

What is described herein is solution polymerization in acetone solvent of a monomer mixture of maleic anhydride, vinyl acetate and isobornyl acrylate or methacrylate.

DETAILED DESCRIPTION OF THE INVENTION

The terpolymer product is a random or alternating structure comprising essentially maleic anhydride, vinyl acetate and isobornyl acrylate or methacrylate. A typical terpolymer composition comprises the monomers, respectively, in a molar ratio of about 0.35–1:1:0.05–0.25, preferably 0.6–0.8:1:0.08–0.12, and, most preferably, 0.75:1:0.1.

The terpolymers resins herein are prepared by a solution polymerization process. The process comprises adding the monomers, individually or premixed, preferably in the above proportions, in acetone solvent for both the monomers and the terpolymer, wherein they are polymerized in the presence of a free radical initiator under conditions of agitation at a temperature of between about 40° and about 90° C., preferably between about 50° and about 70° C. The initiator can be added to the monomer mixture before or after the monomers have been charged into the solution medium. The reaction is carried out under an inert atmosphere which can be maintained by purging with nitrogen to eliminate air and oxygen.

The polymerization reaction is carried under constant agitation over a period of from about 4 to 24 hours, although usually about 4 to 12 hours is sufficient to complete the reaction and form the terpolymer product. At this point, the terpolymer product, which is in the form of the free maleic acid product, can be esterified, hydrolyzed or neutralized. Preferably, the terpolymer is esterified with a $C_4$-$C_5$ alkanol, such as butanol or pentanol, to provide the corresponding mono-butyl maleate derivative. Alternatively, the terpolymer can be hydrolyzed or neutralized, if desired.

The vinyl acetate reactant may be substituted by other vinyl ester monomers. Examples of such vinyl ester monomeric components are those containing 4 to 14 carbon atoms which include vinyl acetate, vinyl propionate, vinyl isobutyrate, vinyl butyrate, vinyl hexanoate, vinyl pivalate, vinyl laurate and vinyl neodecanoate, of which vinyl acetate is the most preferred.

The isobornyl acrylate reactant may be substituted by other acrylate or methacrylate esters, of which suitably acrylate and/or methacrylate esters of isoborneol, exo-norborneol and endo-norborneol are preferred, and the isobornyl ester is the most preferred. The preferred bicyclic compounds are those having a hydrocarbon bridge and are generally defined by the formula

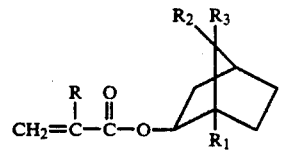

wherein each of R, $R_1$, $R_2$ and $R_3$ is hydrogen or methyl.

The invention will now be described with reference to the following examples.

EXAMPLE 1

Into a four-necked, one-liter resin kettle, fitted with a nitrogen inlet tube, a dropping-funnel, a thermometer, a reflux condenser and a mechanical agitator, was charged 103.2 g. of vinyl acetate (1.2 moles), 154.8 g. of mono-n-butyl maleate (0.9 mole) and 24.96 g. of isobornyl acrylate (0.12 mole). After charging 0.2653 g. of di-ethylhexyl peroxydicarbonate (Lupersol ® 223M75, 75% active) and 282.96 g. of acetone, the reactants were bubbled with nitrogen (150 ml/min.) for 15 minutes. The reactants then were heated gently under agitation (250 rpm) to 49° C. over 20 minutes and then to 58° C.

over the next 10 minutes (mild reflux). The reaction was held at 58°-60° C. for 16 hours while adding 0.2653 g. of Lupersol® 223M75 hourly. At this point, unreacted vinyl acetate was 0.90% by titration. Then 282.96 g. of SDA-40-2 ethanol (95%) was added. Acetone was removed by distillation until the reactant temperature was 74° C. The terpolymer has a resin solids of 50.4%, a relative viscosity of 1.28 and a K value of 32.

The terpolymeric resins thus prepared by solution polymerization are employed as the active ingredient in a non-aerosol pump hair spray formulation and employed in a cosmetic product fitted with a suitable nozzle pump valve. The present resins are employed in concentrations between about 6 to 20% solids, preferably 8 to 15% solids. Such cosmetic products can be used over an extended period of time to generate fine spray mists without experiencing any nozzle clogging.

While the invention has been described with particular reference to certain embodiments thereof, it will be understood that changes and modifications may be made which are within the skill of the art.

Accordingly, it is intended to be bound only by the following claims, in which:

1. A solution polymerization process for the preparation of terpolymers consisting essentially of maleic anhydride, vinyl acetate and isobornyl acrylate or methacrylate wherein said monomers are present in a molar ratio of about 0.35-1:1:0.05-0.25, respectively, which comprises polymerizing said monomers in said proportions in acetone solution.

2. A solution polymerization process according to claim 1 in which the terpolymer product is esterified.

3. A solution polymerization process according to claim 2 in which the terpolymer is esterified with a $C_4$-$C_5$ alkanol.

4. A solution polymerization process according to claim 3 wherein said alkanol is butanol.

5. A solution polymerization process according to claim 1 wherein said molar ratio is about 0.6-8:1:0.08-0.12.

6. A solution polymerization process according to claim 1 in which the polymerization is complete in about 12 hours.

* * * * *